(12) United States Patent
Sanders et al.

(10) Patent No.: US 8,609,353 B2
(45) Date of Patent: Dec. 17, 2013

(54) DIAGNOSTICS AND METHODS FOR REMOVAL AND DETECTION OF INTERFERENTS

(75) Inventors: Mitchell C. Sanders, West Boylston, MA (US); Diane L. Ellis-Busby, Lancaster, MA (US); Jennifer M. Havard, Framingham, MA (US); James C. Comolli, Boxborough, MA (US)

(73) Assignee: Systagenix Wound Management (US), Inc., Wilmington, DE (US)

( * ) Notice: Subject to any disclaimer, the term of this patent is extended or adjusted under 35 U.S.C. 154(b) by 1153 days.

(21) Appl. No.: 12/160,610

(22) PCT Filed: Feb. 2, 2007

(86) PCT No.: PCT/US2007/002985
§ 371 (c)(1),
(2), (4) Date: Feb. 17, 2009

(87) PCT Pub. No.: WO2007/092360
PCT Pub. Date: Aug. 16, 2007

(65) Prior Publication Data
US 2009/0304778 A1    Dec. 10, 2009

(51) Int. Cl.
*G01N 33/53*    (2006.01)
*G01N 31/00*    (2006.01)

(52) U.S. Cl.
USPC ........... 435/7.21; 435/7.1; 436/501; 436/518; 424/9.1; 424/520; 530/300; 530/350

(58) Field of Classification Search
None
See application file for complete search history.

(56) References Cited

U.S. PATENT DOCUMENTS

| 2003/0206944 A1 | 11/2003 | Cohen et al. |
| 2003/0215358 A1 | 11/2003 | Schulman et al. |
| 2004/0142910 A1 | 7/2004 | Vachon et al. |

FOREIGN PATENT DOCUMENTS

| WO | WO 90/07115 | 6/1990 | | |
| WO | WO 90/10232 | 9/1990 | | |
| WO | WO 91/02816 | 3/1991 | | |
| WO | WO 91/02816 A1 | * 3/1991 | .............. | C12Q 1/68 |
| WO | WO 98/09167 | 3/1998 | | |
| WO | WO 02/35216 | 5/2002 | | |
| WO | WO 02/35216 A1 | * 5/2002 | ............. | G01N 21/78 |

OTHER PUBLICATIONS

International Search Report for International Application No. PCT/US2007/002985 with International Filing Date of Feb. 2, 2007.
Edwards, J.V. et al., "Design, preparation and assessment of citrate-linked monosaccharide cellulose conjugates with elastase-lowering activity", Carbohydrate Polymers, Applied Science Publishers, Ltd. 50(3): 305-314, Nov. 15, 2002. XP004395909.

* cited by examiner

*Primary Examiner* — Lisa Cook
(74) *Attorney, Agent, or Firm* — Brian B. Shaw, Esq.; Paul A. Leipold, Esq.; Harter Secrest & Emery LLP

(57) ABSTRACT

Described herein are substrates, methods, articles, and kits that are useful for removing interferents from samples for diagnostic purposes. The interferents are removed with phosphocellulose and cation exchange materials. These materials could also be used in vitro to improve the performance of a diagnostic assay or in vivo to remove the interferents.

32 Claims, 10 Drawing Sheets

| Swab | Elastase μg/ml | Swab | Elastase μg/ml |
| --- | --- | --- | --- |
| 50A | 2.5 | 117 | 1.2 |
| 69 | 2.7 | 118 | 0.3 |
| 71 | 21.7 | 115 | 8.3 |
| 80A | 0.0 | 119 | 1.5 |
| 88 | 46.0 | 120 | 2.2 |
| 91 | 6.4 | 121 | 8.6 |
| 96 | 5.6 | 123 | 5.8 |
| 97 | 0.3 | 125 | 15.3 |
| 98 | 4.5 | 126B | 0.0 |
| 100C | 2.1 | 126A | 10.7 |
| 100D | 7.0 | 127 | 1.2 |
| 102 | 9.3 | 130 | 9.7 |
| 102B | 0.1 | 131 | 3.6 |
| 102C | 3.4 | 132 | 16.2 |
| 102D | 0.1 | 133 | 19.3 |
| 102E | 4.9 | 134 | 29.2 |
| 104 | 16.6 | 135 | 8.5 |
| 105A | 7.1 | 136 | 49.9 |
| 105B | 23.5 | 137 | 6.8 |
| 106 | 60.5 | 138 | 3.1 |
| 107 | 10.5 | 140A | 24.1 |
| 109 | 14.9 | 140B | 0.1 |
| 114A | 5.8 | 141 | 4.8 |
| 114B | 15.5 | 139 | 2.1 |
| 114C | 49.0 | 143 | 6.0 |
| 116 | 2.7 | | |

FIG. 2

SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: HE1-related peptide

<400> SEQUENCE: 1

Pro Phe Pro Gln Ala Asn Tyr Ile Thr Tyr
1               5                   10

<210> SEQ ID NO 2
<211> LENGTH: 9
<212> TYPE: PRT
<213> ORGANISM: Artificial Sequence
<220> FEATURE:
<223> OTHER INFORMATION: PAIN1-related peptide

<400> SEQUENCE: 2

Pro Met Pro Pro Leu Cys Thr Ser Met
1               5

<210> SEQ ID NO 3
<211> LENGTH: 15
<212> TYPE: PRT
<213> ORGANISM: Artificial Sequence
<220> FEATURE:
<223> OTHER INFORMATION: CPI2-related peptide

<400> SEQUENCE: 3

Glu Gly Ala Met Phe Leu Glu Ala Ile Pro Met Ser Ile Pro Lys
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Pseudomonas aeruginosa E8-related peptide

<400> SEQUENCE: 4

Glu Gln Ala Asp Ala Leu His Asp Gln Ala Ser Ala Leu Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Pseudomonas aeruginosa G6-related peptide

<400> SEQUENCE: 5

Glu Ala Ala His Gln Ser Ala Leu Gln Ser Ala Lys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Staphylococcus aureus SAP2-related peptide

<400> SEQUENCE: 6

Glu Thr Lys Val Glu Glu Asn Glu Ala Ile Gln Lys

```
                           1               5                         10

<210> SEQ ID NO 7
<211> LENGTH: 11
<212> TYPE: PRT
<213> ORGANISM: Artificial Sequence
<220> FEATURE:
<223> OTHER INFORMATION: Escherichia coli T2-related peptide

<400> SEQUENCE: 7

Glu Val Ser Arg Arg Arg Arg Arg Gly Gly Lys
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Escherichia coli T3-related peptide

<400> SEQUENCE: 8

Lys Lys Ala Ser Glu Val Ser Arg Arg Arg Arg Arg Gly Gly Lys
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: HE1-related peptide

<400> SEQUENCE: 9

Pro Phe Pro Gln Ala Asn Tyr Ile Thr Tyr Cys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: PAIN-1-related peptide

<400> SEQUENCE: 10

Pro Met Pro Pro Leu Cys Thr Ser Met Lys
1               5                   10
```

DIAGNOSTICS AND METHODS FOR REMOVAL AND DETECTION OF INTERFERENTS

RELATED APPLICATION

This application claims the benefit of U.S. Provisional Application No. 60/764,621, filed Feb. 2, 2006. The entire teachings of the above application are incorporated herein by reference.

BACKGROUND OF THE INVENTION

In diagnostics, immuno-staining, immunochemistry, and ELISA applications, it is often desirable to use enzymes such as horseradish peroxidase (HRP) and alkaline phosphatase (AP) to produce an amplification of the signal through the enzyme turnover of a colored substrate. The color substrates such as TMB (3,3',5,5'-tetramethyl benzidine), ABTS (2,2'azino-bis-(3-ethylbenzthiazoline-6-sulfionic acid), DAB (3,3'-diaminobenzidine tetrahydrochloride), NBT (nitro-blue tetrazolium chloride), and BCIP (5-bromo-4-chloro-3'-indolylphosphate p-toluidine salt) used with these enzymes are commercially available in both soluble and insoluble forms, with various applications in immunochemistry, enzyme assays, and diagnostics. It would be helpful to remove and detect interferents which hinder the efficiency of these applications.

SUMMARY OF THE INVENTION

Although fluids such as saliva and urine have very little cross-reactivity issues with the substrates for AP and HRP, it has been found that more complex fluid samples (including, but not limited to, interferents such as wound fluids or blood) from patients can have a significant concentration of these interferents that can hinder diagnostic investigation. The use of cation exchange materials and, or in combination with phosphocellulose to remove these interferents from wounds and other bodily fluids for the purpose of improving the signal-to-noise ratio of a diagnostic assay, is reported herein.

It would be useful to improve the signal-to-noise ratio in such assays and applications.

This invention encompasses the use of a cation exchange material, such as sulfopropyl (SP) or carboxylmethyl (CM), that can be used at a slightly basic pH (about 7.5-about 8.0) to remove elastase (e.g., human elastase) from wound samples or other specimens (including but not limited to blood, urine, stool or tissue biopsies) that may interfere with any diagnostic assay, including one that is antibody, enzyme, or PCR based. We have found that the cation exchange material can be used in multiple formats (including, but not limited to, beads, membranes, non-woven fibers and/or cotton swabs, sponges, filters, wipes, pads, and dressings) that can remove elastase within seconds prior to the sample being loaded into a lateral flow chamber, dipstick, or any kind of liquid assay including, but not limited to, ELISA, and lateral flow or push through assays in which the colored substrate is soluble or insoluble. In some embodiments, every trace of human elastase is removed.

The material can be placed on, for example, a dressing, pad, or wipe to be used to remove elastase in situ, which may improve wound healing by removing deleterious enzymes, including host enzymes, that prevent healing.

In some embodiments, this invention includes a method of removing at least one interferent from a sample comprising contacting a cation exchange material and/or phosphocellulose to said sample, thereby removing said interferent.

In other embodiments, this invention includes a method of increasing the specificity of an assay of a sample, said sample comprising at least one interferent, comprising contacting a cation exchange material and phosphocellulose to said sample, thereby removing said interferent.

In some embodiments, the interferent is selected from the group consisting of peroxidases, elastase, papain, matrix metalloproteases, heme and viruses.

In some embodiments, the sample is selected from the group consisting of wound, tissue, urine, saliva, blood, and stool samples.

In other embodiments, the sample is selected from the group consisting of fluid, biopsy and solid samples.

In some embodiments, said interferent is peroxidase, and the phosphocellulose is contacted to said sample to remove specifically said peroxidase.

In other embodiments, said interferent is hemoglobin, and the phosphocellulose is contacted to said sample to remove specifically the hemoglobin.

In yet other embodiments, the phosphocellulose is selected from the group consisting of p11 resin and p81 paper.

In some embodiments, the interferent is elastase, and the cation exchange material is contacted to said sample to remove specifically the elastase.

In other embodiments, the cation exchange material is selected from the group consisting of sulfopropyl sepharose and carboxylmethyl sepharose.

In some embodiments, the elastase is capable of detection by a peptide comprising the amino acid sequence of PFPQANYITY (SEQ ID NO: 1).

In other embodiments, the papain is capable of detection by a peptide comprising the amino acid sequence of PMPPLCTSM (SEQ ID NO: 2).

In some embodiments, the assay is selected from the group consisting of an enzyme-based assay, an immunoassay, an immunostaining application, an antibody-based assay, a PCR-based assay, a protease-based assay, a diagnostic test, a push through assay and a lateral flow assay.

In other embodiments, the interferent is removed prior to an immunostaining or a PCR reaction.

In further embodiments, the cation exchange material or phosphocellulose is applied to a gauze, cleansing wipe, bead, glass frit, swab, wipe, pad, membrane, a non-woven fiber, a sponge, a filter, a biopsy punch or a dressing prior to contact to said sample.

In some embodiments, the cation exchange material or phosphocellulose is incorporated into a biopsy punch device prior to contact to the sample.

In other embodiments, the cation exchange material or phosphocellulose is applied to a lateral flow assay device prior to contact to the sample.

In other embodiments, the cation exchange material or phosphocellulose is applied to the back of a swab (e.g., a cotton, polyurethane, or polyester swab), a medical device (e.g., a speculum) or sampling device, As used herein, a sampling device is any device used to acquire a sample from a person (e.g., a patient), such as a fluid or tissue sample. One example of such a device is a wound biopsy device.

In further embodiments, said cation exchange membrane or phosphocellulose is incorporated into a collection container, a collection device, a tube, a vial, or a cassette. In some embodiments, the incorporation occurs prior to diagnostic testing.

In some embodiments, this invention includes a method of increasing the specificity of an assay of a sample, said sample comprising at least one interferent, comprising contacting phosphocellulose to said sample, thereby removing said interferent.

In other embodiments, said interferent is selected from the group consisting of heme and peroxidase.

In other embodiments, this invention includes a method of increasing the specificity of an assay of a sample, said sample comprising at least one interferent, comprising contacting a cation exchange material to said sample, thereby removing said interferent.

In some embodiments, said interferent is elastase.

In some embodiments, this invention includes a method of extracting at least one interferent from fluids in a lateral flow device, comprising contacting a cation exchange membrane or phosphocellulose to said fluid, thereby removing said interferent.

In other embodiments, this invention includes a method of enhancing a signal-to-noise ratio in an assay of a biological sample, wherein the sample contains interferents, comprising contacting a cation exchange material or phosphocellulose to said sample, thereby removing said interferents.

In some embodiments, this invention includes an isolated peptide comprising the amino acid sequence of PFPQANYITY (SEQ ID NO: 1).

In other embodiments, this invention includes an isolated peptide comprising the amino acid sequence of PMPPLCTSM (SEQ ID NO: 2).

The invention described herein also encompasses wound cleansing products, treatment products and wound treatment products.

In some embodiments, this invention includes a wound cleansing product comprising a gauze or wipe, wherein said gauze or wipe contains a cation exchange material, wherein said cation exchange material removes at least one interferent from said wound.

In some embodiments, this invention includes a wound cleansing product comprising a gauze or wipe, wherein said gauze or wipe contains phosphocellulose, wherein said phosphocellulose removes at least one interferent from said wound.

The invention also encompasses kits, including assay kits.

In some embodiments, the assay is selected from the group consisting of an enzyme-based assay, an immunoassay, an immunostaining application, an antibody-based assay, a PCR-based assay, a protease-based assay, a diagnostic test, a push through assay and a lateral flow assay.

In other embodiments, this invention includes a biological assay kit comprising a cation exchange material, wherein said cation exchange material removes at least one interferent from a sample prior to assessment of the sample.

In further embodiments, this invention includes a biological assay kit comprising phosphocellulose, wherein said phosphocellulose removes at least one interferent from a sample prior to assessment of the sample.

In some embodiments, this invention includes a biological assay kit comprising a cation exchange material, phosphocellulose and a diagnostic assay device.

In other embodiments, the diagnostic assay device is selected from the group consisting of a biopsy punch device and a lateral flow device.

In some embodiments, said interferent is removed prior to an immunostaining or a PCR reaction.

In some embodiments, said cation exchange material or phosphocellulose is applied to a gauze, cleansing wipe, bead, glass frit, swab, wipe, pad, membrane, a non-woven fiber, a sponge, a filter, or a dressing prior to contact to said sample.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2 is a table of μg/ml of the concentration of human neutrophil elastase from wound samples.

DETAILED DESCRIPTION OF THE INVENTION

Figure 1:
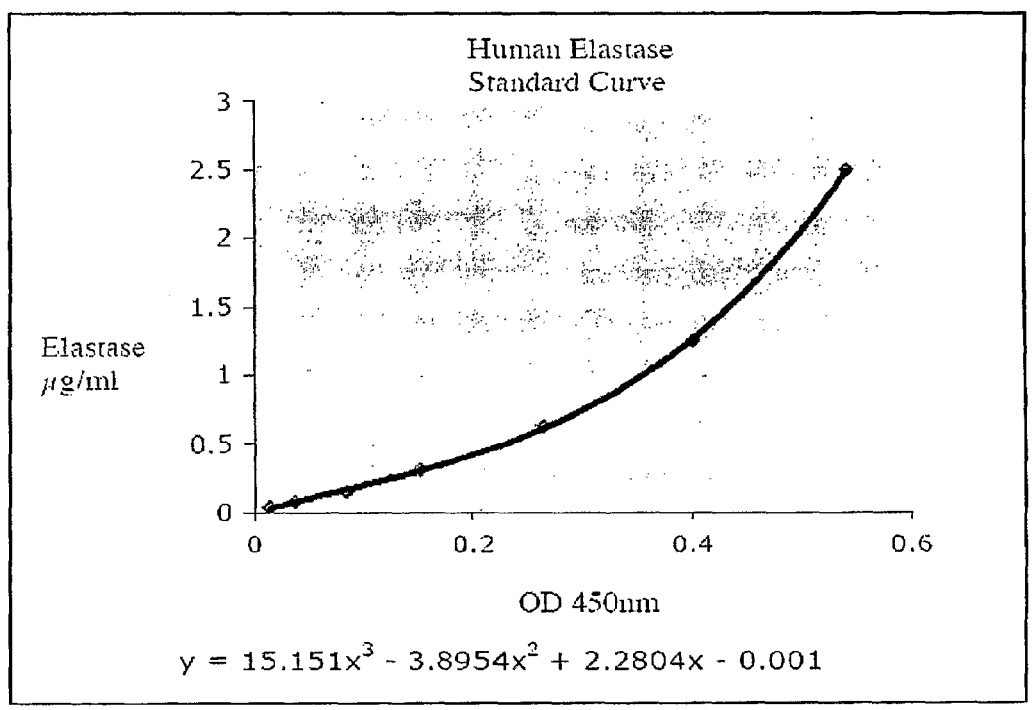
FIG. 1 is a standard curve plot for human neutrophil elastase.

A description of preferred embodiments of the invention follows.

This invention encompasses a method of removing at least one interferent from a sample comprising contacting a cation exchange material or phosphocellulose to said sample, thereby removing said interferent.

As defined herein, the term "interferent" includes, but is not limited to, peroxidases, elastase, papain, matrix metalloproteases, heme, hemoglobin and viruses. An interferent includes matter in a sample which lowers the signal-to-noise ratio of an assay, likely reducing its specificity.

As used herein, the term "phosphocellulose" includes, but is not limited to, p11 resin and p81 paper.

As used herein, the term "cation exchange material" includes, but is not limited to, sepharose such as sulfopropyl sepharose and carboxylmethyl sepharose.

As used herein the term "sample" includes, but is not limited to any biological or bodily sample, for example, a sample obtained from or derived from an animal (e.g., a human). "Samples" include, but are not limited to wound, tissue, exudate, urine, saliva, blood, stool, fluid, biopsy and solid samples.

As used herein, an assay includes, but is not limited to, an enzyme-based assay, an immunoassay, an immunostaining application, an antibody-based assay, a polymerase chain reaction (PCR)-based assay, a protease-based assay, a diagnostic test, a push through assay and a lateral flow assay.

Elastase

Human elastase is produced in wound fluid at a variable concentration of approximately 50 ng-60 µg/1 ml of sample. See Schonfelder, U. et al., "Influence of Selected Wound Dressings on PMN Elastase in Chronic Wound Fluid and Their Antioxidative Potential in Vitro," *Biomaterials*, 26(33): 6664-6673 (2005). Human elastase is a basic protein with an isoelectric point of 8.77 and a molecular weight of 25,685.71 Da. The enzyme, when present in a high concentration in wound fluid (or other tissue samples), can be a problem for antibody, enzyme, or PCR-based diagnostic approaches. In the case of an enzyme-based reporter system that measures a specific protease, elastase can cause false positives, thereby reducing the specificity of such an assay.

Human elastase is a well-characterized enzyme with the active center hydrolyzing between the bonds of non-aromatic uncharged amino acids -$P_1$-$P_1'$. $P_1$ is a nonaromatic uncharged amino acid (such as A,V,L,I,S) and $P_1'$ is any amino acid except proline. See Wiesner, O. et al., "Differences Between Human Proteinase 3 and Neutrophil Elastase and Their Murine Homologues are Relevant for Murine Model Experiments," *FEBS Lett.*, 579(24):5305-5312 (2005) and Getie, M. et al., "Characterization of Peptides Resulting from Digestion of Human Skin Elastin with Elastase," *Proteins*, 61(3):649-657 (2005). Due to the broad specificity of elastase as compared with very specific proteolytic events of bacterial virulence factors, it can be quite labor-intensive to optimize a peptide substrate that will not cross react with elastase and still function as a reporter system for a specific protease. It has now been determined that cationic material may be advantageous for removing human elastase from wound samples as well as tissue and fluid specimens. At a basic pH of about 8.0 and above, most proteins will not bind to a cation exchange resin, but human elastase can be specifically removed from the sample.

Peroxidases

Human fluids contain a number of peroxidases, most notably glutathione peroxidases, myeloperoxidases, and eosinophil peroxidases. Peroxidases have been purified using a variety of methods including ion exchange, concavalin A (Con A), and hydrophobic interaction chromatography. See Anspach, F. B. et al., "High-Performance Liquid Affinity Chromatography with Phenylboronic Acid, Benzamidine, Tri-L-Alanine, and Concanavalin A Immobilized on 3-Isothiocyanatopropyltriethoxysilane-Activated Nonporous Monodisperse Silicas," *Anal. Biochem.*, 179(1):171-181 (1989); Bozeman, P. M. et al., "Inhibition of the Human Leukocyte Enzymes Myeloperoxidase and Eosinophil Peroxidase by Dapsone," *Biochem. Pharmacol*, 44(3):553-563 (1992); Coval, M. L. and Taurog, A., "Purification and Iodinating Activity of Hog Thyroid Peroxidase," *J. Biol. Chem.*, 242(23):5510-5523 (1967); Gardas, A. et al., "Distinct Immunological and Biochemical Properties of Thyroid Peroxidase Purified from Human Thyroid Glands and Recombinant Protein Produced in Insect Cells," *Biochim. Biophys. Acta.*, 1433(1-2):229-239 (1999); Hope, H. R. et al., "Large-Scale Purification of Myeloperoxidase from HL60 Promyelocytic Cells: Characterization and Comparison to Human Neutrophil Myeloperoxidase," *Protein Expr. Purif.*, 18(3):269-276 (2000); Husereau, D. R. and Suresh, M. R., "A General Affinity Method to Purify Peroxidase-Tagged Antibodies," *J. Immunol. Methods*, 249(1-2): 33-41 (2001); Langbakk, B. and Flatmark, T., "Demonstration and Partial Purification of Lactoperoxidase from Human Colostrum," *FEBS Lett.*, 174(2):300-303 (1984); Matheson, N. R. et al., "Isolation and Properties of Human Neutrophil Myeloperoxidase," *Biochemistry*, 20(2):325-330 (1981); Merrill, D. P., "Purification of Human Myeloperoxidase by Concanavalin A-Sepharose Affinity Chromatography," *Prep. Biochem.*, 10(2):133-150 (1980); and Olsen, R. L. and Little, C., "Purification and Some Properties of Myeloperoxidase and Eosinophil Peroxidase from Human Blood," *Biochem. J.*, 209(3): 781-787 (1983). These references are incorporated herein by reference in their entirety.

The following additional references are incorporated herein by reference in their entirety: Matheson, N. R. et al., "Interaction of Human Alpha-1-Proteinase Inhibitor with Neutrophil Myeloperoxidase," *Biochemistry*, 20(2):331-336 (1981); Dumer, J. and Klessig, D. F., "Inhibition of Ascorbate Peroxidase by Salicylic Acid and 2,6-Dichloroisonicotinic Acid, Two Inducers of Plant Defense Responses," *Proc. Natl. Acad. Sci. USA*, 92(24):11312-11316 (1995); Fortunato, S. J. et al., "Anmiotic Fluid Concentrations of Collagenase-1 and Collagenase-3 are Increased in Polyhydramnios," *J. Perinat. Med.*, 32(2):122-125 (2004); and Kettle, A. J. et al., "Mechanism of Inactivation of Myeloperoxidase by 4-Aminobenzoic Acid Hydrazide," *Biochem. J.*, 321:503-508 (1997); and Lobmann, R. et al., "Expression of Matrix-Metalloproteinases and Their Inhibitors in the Wounds of Diabetic and Non-Diabetic Patients," *Diabetologia*, 45(7):111-1016 (2002).

Peroxidases can interfere with assays that use HRP as the reporter enzyme. In addition to these enzymes, we have found that heme in blood can also cause non-specific colorization of the substrate, thereby producing some false positives. Although there is a commercial polyelectrolyte available to remove hemoglobin from diagnostic assays (HEMAGLOBIND™, Biotech Support Group, NJ, U.S. Pat. No. 5,294,681), our findings indicate that HEMAGLOBIND™, only removes about 50% of the peroxidase-like interferents in human wound samples. Using a screen for materials that would efficiently remove peroxidases from human samples, we have determined that phosphocellulose (P11, P81, Whatman plc, Brentford, United Kingdom) and a cation exchange membrane (such as CM, SP) are the most effective at removing endogenous peroxidases and hemoglobin. We have demonstrated that cation exchange material such as SP-sepharose beads (GE Life Sciences) will remove elastase and peroxidases with a basic isoelectric point and the P11 or phosphocellulose material will also remove heme from wounds or blood samples that would interfere with the color reactions of an alkaline phosphatase or horseradish peroxidase-based assay. The phosphocellulose binds and removes proteases.

In some embodiments, peroxidase activity (e.g., of blood) can be removed by shifting the pH of the assay conditions to favor the activity of HRP (for example, to pH of 4.0). At a low pH, HRP strongly reacts with the ABTS substrate whereas the peroxidase activity from blood is minimal. For example, the pH can be shifted to a range of approximately 3-7.5, for example, approximately 3.5-4.5, for example, approximately 4.

Peptides

The invention also encompasses peptides which recognize interferents. Examples of suitable peptides include the sequence PFPQANYITY (referred to herein as SEQ ID NO: 1) and the sequence PMPPLCTSM (referred to herein as SEQ ID NO: 2) and/or a modified peptide, for example, one containing one or more conserved amino acid substitutions, and peptides that incorporate or comprise SEQ ID NO: 1 and/or SEQ ID NO: 2 or a modified peptide described herein.

Examples of peptides include those described herein, as well as those peptides known in the art to undergo modification by interaction with a protein. For example, U.S. patent application Ser. No. 11/036,761, filed Jan. 14, 2005, by Mitchell C. Sanders, entitled A Device for Detecting Bacterial Contamination and Method of Use; U.S. patent application Ser. No. 10/502,882, which is the U.S. National Stage of International Application Number PCT/US03/03172 filed on Jan. 31, 2003, and International Application Number PCT/US2004/036469 filed on Nov. 3, 2004, describe such peptides and their teachings are incorporated herein by reference in their entirety.

Such peptides described herein can be synthesized from commercial sources, such as New England Peptide (Gardner, Mass.), Sigma-Aldrich, Corp. (St. Louis, Mo.) or Molecular Probes (Eugene, Oreg.), or can be produced (e.g., isolated, purified, or synthesized) using methods known to those of skill in the art.

In some embodiments, the peptides are specific to interferents, i.e., they recognize interferents significantly more that they recognize other proteins in a sample. In some embodiments, the peptides are highly specific, for example, they recognize an interferent but they do not detectably recognize other enzymes in a sample.

In some embodiments, additional side groups are attached to one of the amino acids of the peptide chain. For example, a substrate of the invention can include a benzyl ether protecting group bound to one or more of the serine acids on the peptide chain. Protecting groups are chemical groups that are used to protect an amino acid from reacting with a colorimetric component. The use of protecting groups allows for labeling of the same type of amino acid in one peptide with two colorimetric components. For example, one serine group in a peptide can be protected with a benzyl ether group and a second serine, which is not protected, can be reacted with one colorimetric component. The protecting group can be removed and the second serine can be reacted with a different color component, thereby creating a substrate with two different color components.

In some embodiments, when the peptides herein can be coupled to a reporter (e.g., an enzyme or a dye), a cysteine ("C") is added to the carboxyl terminal of the peptide. For example, the HE1 peptide, when coupled to a reporter, is H$_2$N-PFPQANYITYC-OH (SEQ ID NO: 9).

In other embodiments, when the peptides are used in a FRET assay, amino acids can be appended to the termini of the peptides to introduce the dyes. For example, an "E" is added to the amino terminal and a "K" is added to the carboxyl terminal For example, when the PAIN1 peptide is used in the FRET assay, an "E" is added to the N terminal and a "K" is added to the C terminal, (NH$_2$-E(Edans) PMPPLCTSMK (Dabcyl)-COOH) (SEQ ID NO: 10).

The peptides of the invention also encompass fragments and sequence variants of the peptides described herein. Variants include a substantially homologous peptide encoded by the same genetic locus in an organism, i.e., an allelic variant, as well as other variants. Variants also encompass peptides derived from other genetic loci in an organism. Variants also include peptides substantially homologous or identical to these peptides but derived from another organism and or D and L isomers (i.e., an ortholog), produced by chemical synthesis, or produced by recombinant methods.

In some embodiments, the peptide that undergoes modification through interaction with a protein comprises an amino acid sequence, such as one of the sequences listed herein or a sequence having at least 50%, 60%, 70%, 80%, 85%, 90%, 95%, or 99% sequence identity to one of the sequences listed herein, as determined using a sequence comparison program and parameters described herein.

The percent identity of two amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions×100). In certain embodiments, the length of the amino acid sequence aligned for comparison purposes is at least 30%, preferably, at least 40%, more preferably, at least 60%, and even more preferably, at least 70%, 80%, 90%, or 100% of the length of the reference sequence. The actual comparison of the two sequences can be accomplished by well-known methods, for example, using a mathematical algorithm. A preferred, non-limiting example of such a mathematical algorithm is described in Karlin, S., et al., "Unusual Charge Configurations in Transcription Factors of the Basic RNA Polymerase II Initiation Complex," *Proc. Natl. Acad. Sci. USA,* 90(12):5593-5597 (1993), which is incorporated herein by reference. Such an algorithm is incorporated into the BLAST programs (version 2.2) as described by Schäffer, A. A. et al., "Improving the Accuracy of PSI-BLAST Protein Database Searches With Composition-Based Statistics and Other Refinements," *Nucleic Acids Res.,* 29:2994-3005 (2001), which is incorporated herein by reference. When utilizing BLAST and Gapped BLAST programs, the default parameters of the respective programs can be used. In one embodiment, the database searched is a non-redundant database, and parameters for sequence comparison can be set at: no filters; Expect value of 10; Word Size of 3; the Matrix is BLOSUM62; and Gap Costs have an Existence of 11 and an Extension of 1.

In another embodiment, the percent identity between two amino acid sequences can be determined by using the GAP program in the GCG software package (available from Acceirys, Inc. of San Diego, Calif., at http://www.accelrys.com, as of Aug. 31, 2001) using either a Blossom 63 matrix or a PAM250 matrix, and a gap weight of 12, 10, 8, 6, or 4 and a length weight of 2, 3, or 4. In yet another embodiment, the percent identity between two amino acid sequences can be determined using a gap weight of 50 and a length weight of 3. Other preferred sequence comparison methods are described herein.

The invention also encompasses peptides having a lower degree of identity but having sufficient similarity so as to perform one or more of the same functions performed by a peptide encoded by a nucleic acid molecule of the invention (e.g., the ability to act as a substrate for a protein, e.g., a protein produced by a microorganism). Similarity is determined by conserved amino acid substitution. Such substitutions are those that substitute a given amino acid in a peptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al, "Deciphering the Message in Protein Sequences: Tolerance to Amino Acid Substitutions," *Science*, 247(4948):1306-1310 (1990), which is incorporated herein by reference.

Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncations or a substitution, insertion, inversion, or deletion in a critical residue or critical region.

Amino acids in a peptide of the present invention that are essential for modification of a substrate can be identified by methods known in the art, such as site-directed mutagenesis or alanine-scanning mutagenesis. See Cunningham, B. C. and Well, J. A., "High-Resolution Epitope Mapping of hGH-Receptor Interactions by Alanine-Scanning Mutagenesis," *Science*, 244:1081-1085 (1989), which is incorporated herein by reference. The latter procedure introduces a single alanine mutation at each of the residues in the molecule (one mutation per molecule).

The invention also includes peptide fragments of the amino acid sequence of the various above-mentioned peptides or functional variants thereof. Useful fragments include those that retain the ability to act as substrates for a protein (e.g., a protein produced by a microorganism.

Fragments can be discrete (not fused to other amino acids or peptides) or can be within a larger peptide. Further, several fragments can be comprised within a single larger peptide. In one embodiment, a fragment designed for expression in a host can have heterologous pre- and pro-peptide regions fused to the amino terminus of the peptide fragment and an additional region fused to the carboxyl terminus of the fragment.

The peptide can be produced using standard recombinant protein techniques. See Ausubel, F. M. et al., eds., "Current Protocols in Molecular Biology," (John Wiley & Sons) (1998), the entire teachings of which are incorporated herein by reference). By testing peptide variants with a purified protease, a more specific peptide can be defined, if so desired.

Peptides can be synthesized and conjugated with an enzyme (such as horseradish peroxidase (HRP), alkaline phosphatase (AP) or phenyl oxidase (PO)) or simple dye molecule (e.g., blue dye #1) that allows for the determination of both the sensitivity and the specificity of a peptide for a particular microorganism. The choice of reporter dye dictates the speed of the diagnostic assay. For example, for conjugation to HRP, a 3-step process can be used: 1) labeling HRP with sulfosuccinimidyl-4-(N-maleimidomethyl)cyclohexane-1-carboxylate (SMCC) in sodium phosphate buffer, pH 7.5 to produce a maleimide form; 2) conjugation of HRP maleimide to the peptide in phosphate buffer with 5 mM EDTA; and 3) coupling the HRP-peptide to microbeads. The coupling of the HRP peptide to the micro-beads is performed with the crosslinker, EDC(N-Ethyl-N'-(3-dimethylaminopropyl)carbodiimide hydrochloride) in MES buffer. EDC conjugates the carboxyl groups on the bead to the amino terminus of the peptide. In the case of the slow reacting food grade dye, blue dye 1 can be synthesized with a maleimide to conjugate directly to the cysteine at the C-terminus of the peptide.

Lateral Flow

The cationic exchange and phosphocellulose materials can be incorporated into a lateral flow device. In addition to liquid phase assays, a lateral flow format provides a simple and rapid point-of-care diagnostic. In one embodiment, the device can have four components: a lateral flow strip (1), a conjugate membrane (2), a substrate line (3), and a wicking pad (4). The conjugate pad will likely be a glass microfiber membrane and will be printed with, for example, the HRP-peptide-beads. The glass microfiber slows the flow of the liquid, thereby allowing time for the microbial protease to react with the HRP-peptide-beads. The lateral flow membrane transfers the released HRP to the printed substrate (naphthol) and the wicking membrane at the back of the device acts as a sink to drive the liquid flow through the device. As the HRP reaches the naphthol substrate, the substrate turns blue and forms a line on the lateral flow membrane. The naphthol substrate can slowly diffuse, preventing the formation of a very distinct line. Dissolving the naphthol in Colloidon (2% nitro-cellulose in amyl acetate) is sufficient to keep the line in place. In some embodiments, the materials can be incorporated into the conjugate membrane or incorporated into the swab materials. In some embodiments, it is possible to print the materials on the same strip and separate the chemistries by forming channels. In another embodiment, each chemistry is printed on a separate lateral flow membrane and then three strips can be laminated together in the final device.

The present invention will now be illustrated by the following Examples, which are not intended to be limiting in any way.

EXAMPLES

Example 1

It is possible to determine the concentration of elastase in human wound fluids based on a standard curve for the concentration of active elastase in a sample (FIG. 1). The standard curve for human elastase is shown using the Hbt Human Elastase ELISA kit from Hycult Biotechnology (The Netherlands). The human neutrophil elastase used as the standard is from Athens Research & Technology (Athens, Ga.). Human wound fluid was collected on a polyester swab and then extracted with 1.5 ml of phosphate buffered saline (pH 7.5) (designated by swab number) for testing in the Hbt Human Elastase ELISA kit from Hycult following the kit instructions. The elastase standard curve from FIG. 1 was used to convert assay results into µg/ml of elastase in FIG. 2. A small aliquot of the fluid was used so that the amount of elastase would be in the range of our standard curve, 0-3 µg/ml. A few of the very high elastase samples were diluted 1:10 so that they would be in the range as well. The highest amount of elastase obtained from the samples was 60.5 µg/ml (from sample #106) (FIG. 2).

Example 2

Figure 3:
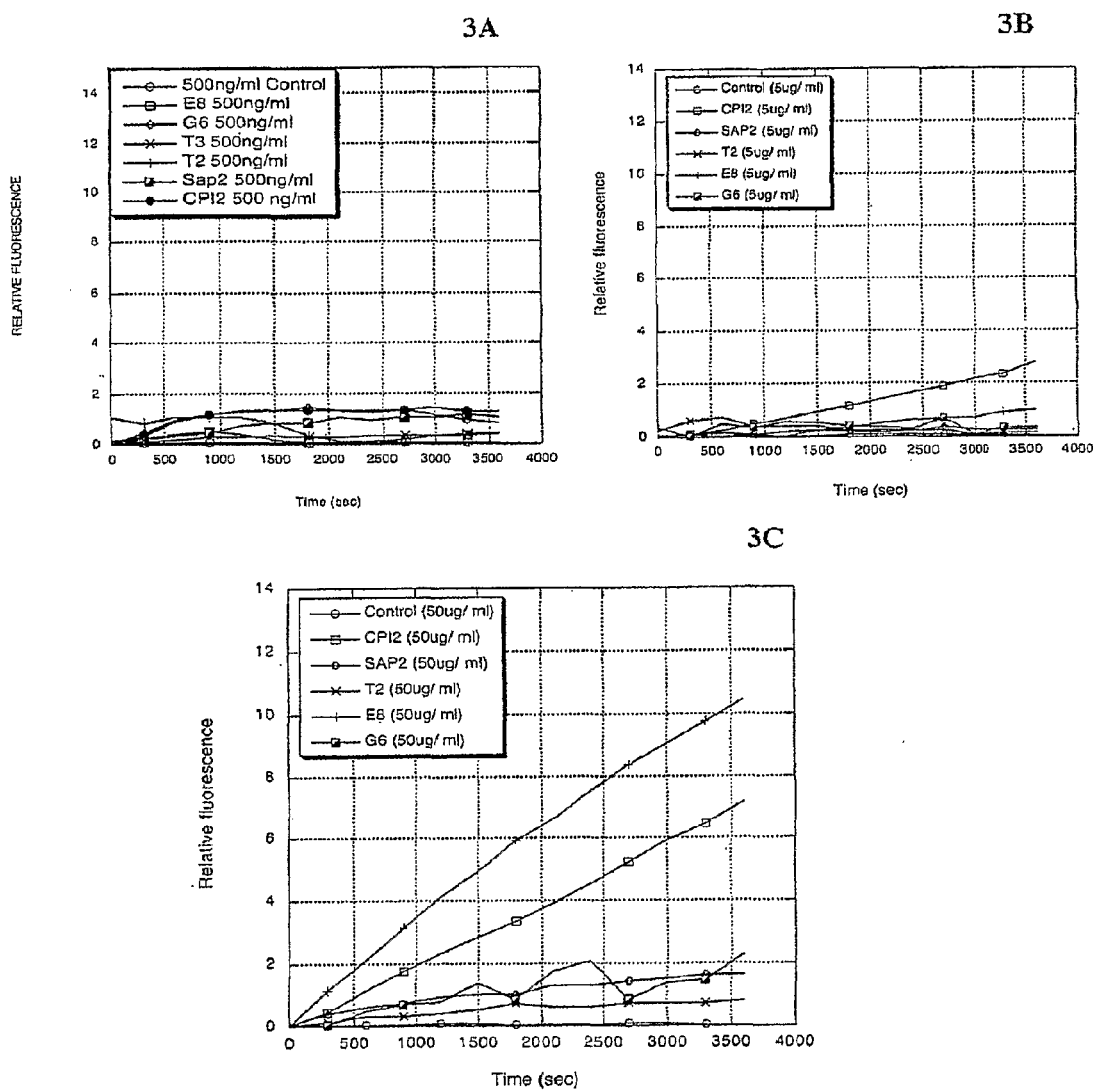
FIG. 3A is a plot graph of the cross-reactivity of specific peptide substrate targets with human elastase.
FIG. 3B is a plot graph of the cross-reactivity of specific peptide substrate targets with human elastase.
FIG. 3C is a plot graph of the cross-reactivity of specific peptide substrate targets with human elastase.

Based on the concentration of elastase from human wound fluid, it was determined whether this amount of elastase (0-50 µg/ml) would cause false positives in a protease assay using fluorescence resonance energy transfer (FRET) with peptides that are specific substrates for bacteria (FIGS. 3A-3C). Broad spectrum pathogen peptides such as CPI2 (peptide sequence EGAMFLEAIPMSIPK (referred to herein as SEQ ID NO:

3)) (that reacts with *Staphylococcus aureus, Proteus mirabilis, Pseudomonas aeruginosa, Enterococcus faecalis*, and *Streptococcus pyogenes*) were studied. Specific peptides for *Pseudomonas aeruginosa* (E8 (peptide sequence EQADAL-HDQASALK (referred to herein as SEQ ID NO: 4)) and G6 (peptide sequence EAAHQSALQSAK (referred to herein as SEQ ID NO: 5))), *Staphylococcus aureus* (SAP2 (peptide sequence ETKVEENEAIQK (referred to herein as SEQ ID NO: 6)), *Escherichia coli* (T2 (peptide sequence EVSR-RRRRGGK (referred to herein as SEQ ID NO: 7)) and T3 (peptide sequence KKASEVSRRRRRGGK (referred to herein as SEQ ID NO: 8)) were also studied. The pathogens were tested with three concentrations of human neutrophil elastase. The peptide substrates were tested in the FRET format with the fluorescent dye Edans attached to one end of the peptide and the quencher Dabcyl attached to the other end of the peptide. In this FRET assay format, amino acids are added to the terminals of the peptides to introduce the FRET assay dye. For example, an "E" is added to the N terminal and a "K" is added to the C terminal. For example, the "E" can be (E-EDANS) and the "K" can be (K-Dabcyl). Cleavage of the peptide substrate by human neutrophil elastase will produce a fluorescent signal. The data in FIG. 3A shows no signal on any of the peptides when tested with 500 ng/ml of elastase. Five µg/ml of elastase cross-reacted with the broad spectrum peptide CPI2 (small response) (FIG. 3B) and 50 µg/ml of elastase cross-reacted with both peptides CPI2 and E8 (FIG. 3C).

E8 is also known as PAE8. G6 is also known as PAG6. In T3, "KKAS" serves as a linker.

These findings indicate that human elastase in a wound sample can interfere with some protease-based detection systems. Therefore, it is important to find material that can be used to suppress the activity of human elastase in order to reduce the number of false positives that can otherwise occur.

Example 3

Figure 4:
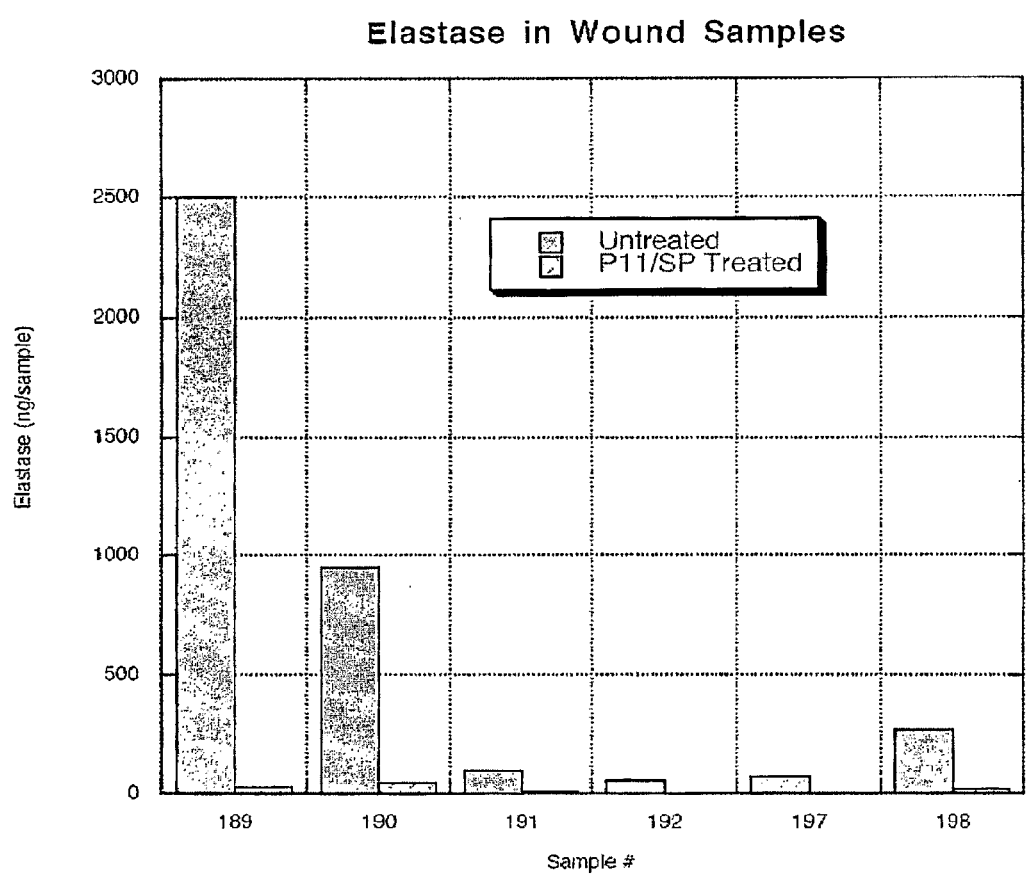
FIG. 4 is a bar graph of the amount of elastase detected in untreated wound fluid and pretreated wound fluid.

FIG. 4 demonstrates the removal of interfering human elastase activity from wound samples by pretreatment with cation exchange resin (such a SP sepharose and phosphocellulose (P11) resins)). Wound samples with a range of elastase concentrations were chosen to test removal by SP/P 11 resin treatment of the samples. 5 µl of the swab samples were treated with 40 µl of a 50% slurry of SP/P11 (50:50) and 75 µl of PBS. The samples were incubated for 5 minutes at room temperature and the resin removed by centrifugation. The elastase concentrations before and after SP/P11 treatment were determined using the Hycult ELISA assay and shown as ng of elastase per sample. Untreated and treated samples were diluted such that the results were on the standard curve of the Hycult ELISA assay. FIG. 4 shows efficient removal of human elastase from six wound samples. After pretreating sample 189 with the P11/SP slurry, the amount of detectable elastase was less than 50 ng/sample.

The findings in FIG. 4 suggest that wound samples pretreated with P11/SP resin prior to diagnostic procedures would have very little non-specific cross reactivity due to human elastase. Earlier attempts to remove elastase using sodium azide led to the inactivation of other enzymes such as horseradish peroxidase. It has also been found that P11/SP resin is capable of removing peroxidase activity.

Prior to developing the P11/SP method to remove elastase cross-reactivity, a library of peptides was screened to develop peptide sequences that would be specific for bacteria but would not cross react with elastase or another enzyme, papain (that is used in the enzymatic debridement of wounds). Peptide sequences that were specific for both elastase and papain were identified.

Example 4

Figure 5:
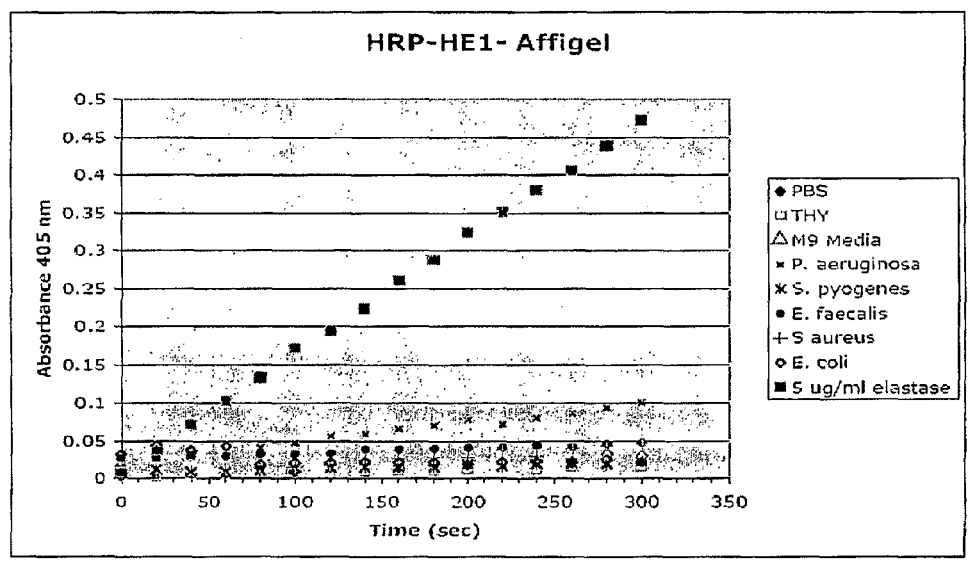
FIG. 5 is a plot graph of the activity of the peptide HE1 ($H_2N$-PFPQANYITYC-OH) (SEQ ID NO: 9) versus specific protease targets.

As shown in FIG. 5, a peptide specific for elastase, HE1, was designed from a high throughput peptide library screen. The peptide was tested for activity by conjugating one end to Affigel 10 beads (BioRad) and the other end to HRP reporter enzyme. The sequence of the HE1 peptide used for this assay was $H_2N$-PFPQANYITYC-OH) (SEQ ID NO: 9). The activity was measured by detecting the release of HRP from the beads in a spin through assay. Testing was performed with 20 µl of a 1:10 dilution of HE1-Affigel beads reacted with 5 µg/ml elastase in 200 µl total volume for 5 minutes. The supernatant above the beads was tested for HRP release (10 µl in 490 µl ABTS substrate) and a clear signal was seen at 405 nm over 5 minutes.

Specificity was tested with 20 µl of a 1:10 dilution of the Affigel beads reacted with 100 µl media control or overnight grown culture of *Pseudomonas aeruginosa, Streplococcus pyogenes, Escherichia coli*, and *Enterococcus faecalis* in 200 µl total volume, as described above. The samples were spun down and a 20 µl aliquot measured in 500 µl total volume ABTS over 5 minutes. The supernatant (or supernatant and cells for *E. Coli*) above the beads was tested for HRP release (10 µl in 490 µl ABTS substrate) and the only signal seen was very minor increase with *Pseudomonas aeruginosa* at 405 nm over 5 minutes.

Example 5

Figure 6:
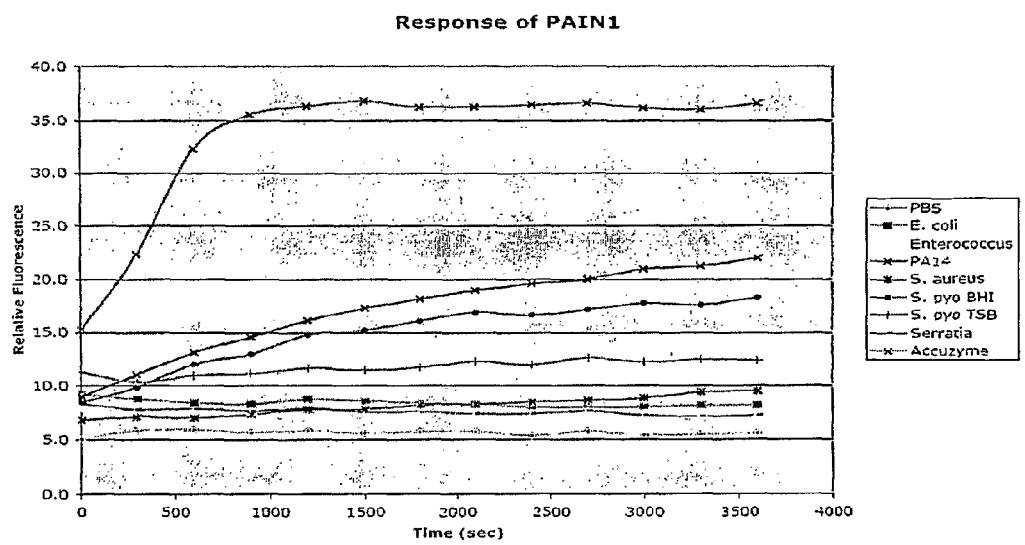
FIG. 6 is a plot graph of the reactivity, as demonstrated by relative fluorescence, of the peptide PAIN1 ($NH_2$-E(Edans)PMPPLCTSMK(Dabcyl)-COO11) (SEQ ID NO: 10) with specific protease targets. At the farthest time points (past 3500 sec.), the top data line indicates ACCUZYME®, the next data line indicates PA14 and the next data line indicates S. pyo BHI.

Using a similar approach, a peptide that was found to detect the presence of papain was derived and called PAIN1 (FIG. 6). PAIN1 was designed from a high throughput screen. The peptide was tested in the FRET format with the fluorescent dye Edans attached to one end of the peptide and the quencher Dabcyl attached to the other end of the peptide. The sequence of the PAIN1 peptide used for this assay was $NH_2$-E(Edans) PMPPLCTSMK(Dabcyl)-COOH (SEQ ID NO: 10). Cleavage of the peptide substrate by papain will produce a fluorescent signal. The peptide was tested using 5 µl of a 5 mg/ml solution with 10 µl of overnight grown bacterial culture or with 10 µl of 120 mg/ml ACCUZYME®, a papain-containing debriding ointment (DPT Laboratories), in 100 µl total volume. The bacteria cultures tested were *Pseudomonas aeruginosa* (PA14), *Streptococcus pyogenes* (grown in BHI and TSB media), *E. coli, Enterococcus faecalis*, and *Serratia marcesens*. The relative fluorescence is shown over one hour. A high response was seen with papain ointment, but there was a lack of specificity since *P. aeruginosa* and *S. pyogenes* cultures produce lower but significant responses. Unlike the elastase peptide HE1 that was found to be specific and not cross react with bacterial proteases, the peptide PAIN1 was found to have a strong signal for papain but found to cross-react with microbial proteases. In particular, the bacteria that appear to cross-react the most with PAIN1 were *Pseudomonas aeruginosa* and *Streptococcus pyogenes*.

Example 6

Figure 7:
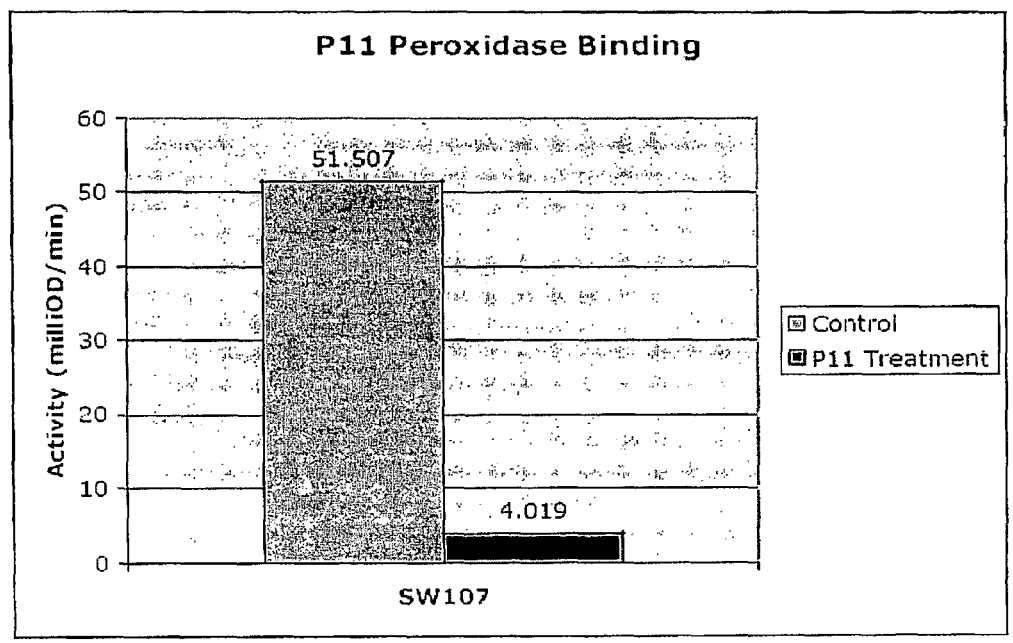
FIG. 7 is a bar graph demonstrating the detection and removal of peroxidases. The left bar (clear) indicates the control and the right bar (filled) indicates P11 treatment.

In addition to elastase being problematic for diagnostic assays, animal peroxidases, papain, and matrix metalloproteases can also cause problems, particularly when horseradish peroxidase is used as a reporter enzyme. In an effort to remove animal peroxidases from animal samples, a number of charged (SB6407, ICE, Biodyne C, Biodyne B, P11), uncharged (P4), and hydrophobic (C8 and C18) membranes were screened to determine if they could remove peroxidase activity. Results indicate that the only material successful at removing peroxidases was P11 phosphocellulose. Wound fluids from a pig have considerable peroxidase activity that can be suppressed by pretreatment of the sample with P11 (FIG. 7). Fluid from a porcine partial thickness wound was collected with a pipet and then the peroxidase activity was measured using the substrate ABTS containing 1 mM hydrogen peroxide. The end point of the blue color was read in a spectrophotometer at 405 nm. The inherent peroxidase activity of one wound sample, sw107 was tested before and after treatment with P11 resin. 40 µl of a 50% slurry of P11 was added to 75 µl of PBS and 5 µl of sw107 and incubated for 5 minutes at room temperature. The resin is removed by centrifugation. 50 µl of the treated sample and the same dilution of untreated sample were assayed in 150 µl of ABTS peroxidase substrate. The slope of the ABTS response was shown in milliOD/min and the effective removal of peroxidase activity was shown after P11 treatment. Pretreatment with P 11 reduced the signal of the peroxidase to 12.5 times lower that the untreated sample (FIG. 7).

Example 7

If a drop of human wound fluid is placed on a dried naphthol substrate on a lateral flow membrane, the human peroxidase activity is visible as a purple spot that discolors the surface of the membrane. If the human wound samples are pretreated with a slurry of P11/SP resin, then the peroxidase activity is undetectable using the same spot assay that showed the pretreated sample. Specifically, clinical samples 212 and 226 had residual peroxidase activity (left panel) that could be removed after pretreatment with the P11/SP resin (right panel).

More specifically, the figure demonstrates the detection and removal of human peroxidases from wound fluids. A 50:50 mixture was made of a 40 mg/ml 4 chloro-1-naphthol (Pierce) solution and 2% Collodion in amyl acetate (Electron Microscopy Sciences). A 10 µl spot of this mixture was placed in the center of a lateral flow membrane (K membrane, Porex) and allowed to dry overnight. For peroxidase testing, a positive and negative control were used. A 1 ng HRP standard (in 10 µl) was placed onto the naphthol spot along with 10 µl of a 3% hydrogen peroxide solution and a light purple spot develops color. 10 µl of 1:10 of an artificial wound fluid (AWF) solution was used as a negative control with 10 µl of a 3% hydrogen peroxide solution. Next, 10 µl of wound fluid sample extracted from a swab is also placed onto a naphthol spot along with 10 µl of a 3% hydrogen peroxide solution. These samples are labeled as 212 un and 226 un. The same wound fluid samples that have been treated with SP and P11 for 5 minutes and then filtered, are also tested on naphthol spots in the same manner: 10 µl of the SP/P11 treated wound fluid sample with 10 µl of a 3% hydrogen peroxide solution. These samples are labeled as 212 tr and 226 tr.

Example 8

Figure 8:
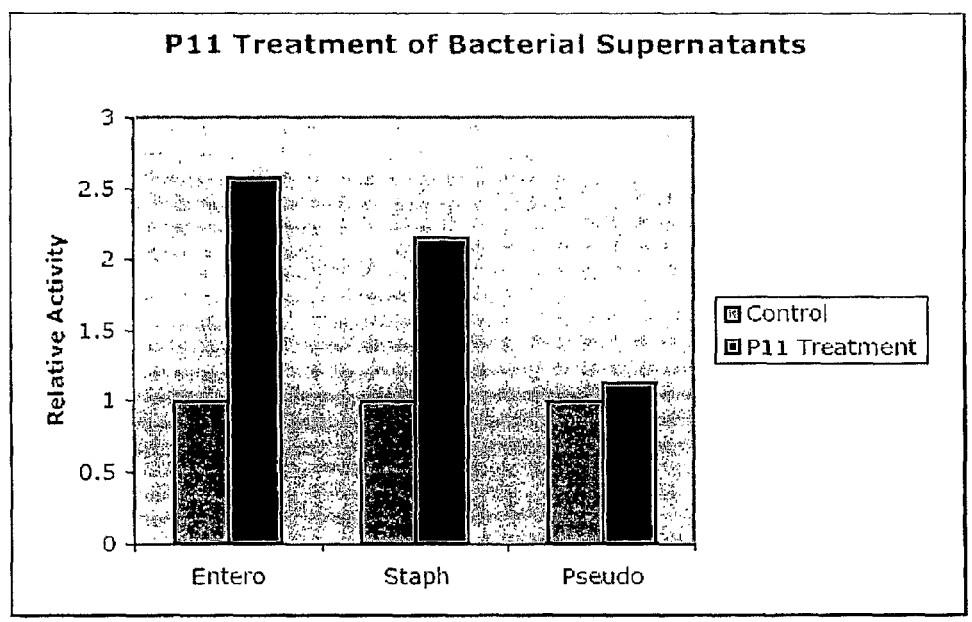
FIG. 8 is a bar graph of the activity of control wound fluid containing bacterial protease versus P11 phosphocellulose-treated wound fluid containing bacterial protease. The left bars (lighter color) indicate control and the right bars (darker color) indicate P11 treatment.
Figure 9:
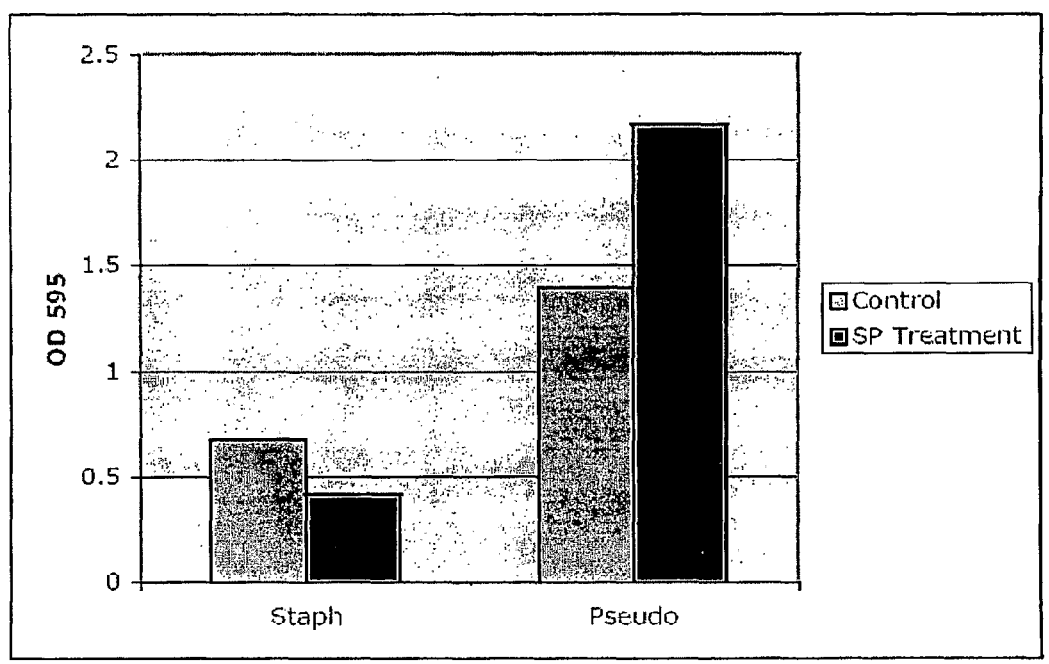
FIG. 9 is a bar graph of the activity of control wound fluid containing bacterial protease versus SP sepharose-treated wound fluid containing bacterial protease. The left bars (lighter color) indicate control and the right bars (darker color) indicate P11 treatment.

Although removal of interferents such as elastase and peroxidase prior to immunostaining, ELISA, or diagnostic assays is important, it is equally important that the P11 and SP materials do not bind the other proteins in the fluid. FIGS. 8 and 9 demonstrate that the bacterial proteases added to the wound fluid are not bound by the pretreatment with P11 and SP. It was found that P11/SP removes molecules that reduce the activity of the enzymes, thereby providing more signal after P11/SP treatment. These results indicate that, although P11 and SP can remove very basic proteins such as elastase and peroxidase, in contrast, most neutral or acidic proteins are unaffected by the pretreatment.

More specifically, the graph in FIG. 8 demonstrates that P11 and SP resins did not remove bacterial proteases. A 50% slurry of P11 resin in water was used. A 40 µl aliquot of P11 slurry was mixed with 10 µl of overnight grown bacterial supernatant (from *Staphylococcus aureus*, *Pseudomonas aeruginosa*, and *Enterococcus faecalis*) and 110 µl PBS. The P11 was given 5 minutes to bind with mixing. The resin was then removed by centrifugation and the bacterial supernatants were tested before and after treatment (with the same dilutions) for activity in the ECI Express Detect system. The released HRP enzyme activity was measured with ABTS substrate. The activity of the bacterial supernatants prior to P11 treatment was normalized to one and the relative activity after P11 treatment is shown in FIG. 8. The same method was used to demonstrate that SP resins did not remove bacterial proteases. The activity of the bacterial supernatants before and after SP treatment is shown in FIG. 9 in terms of an endpoint OD 405 nm measurement of the ABTS substrate.

Example 9

Figure 10:
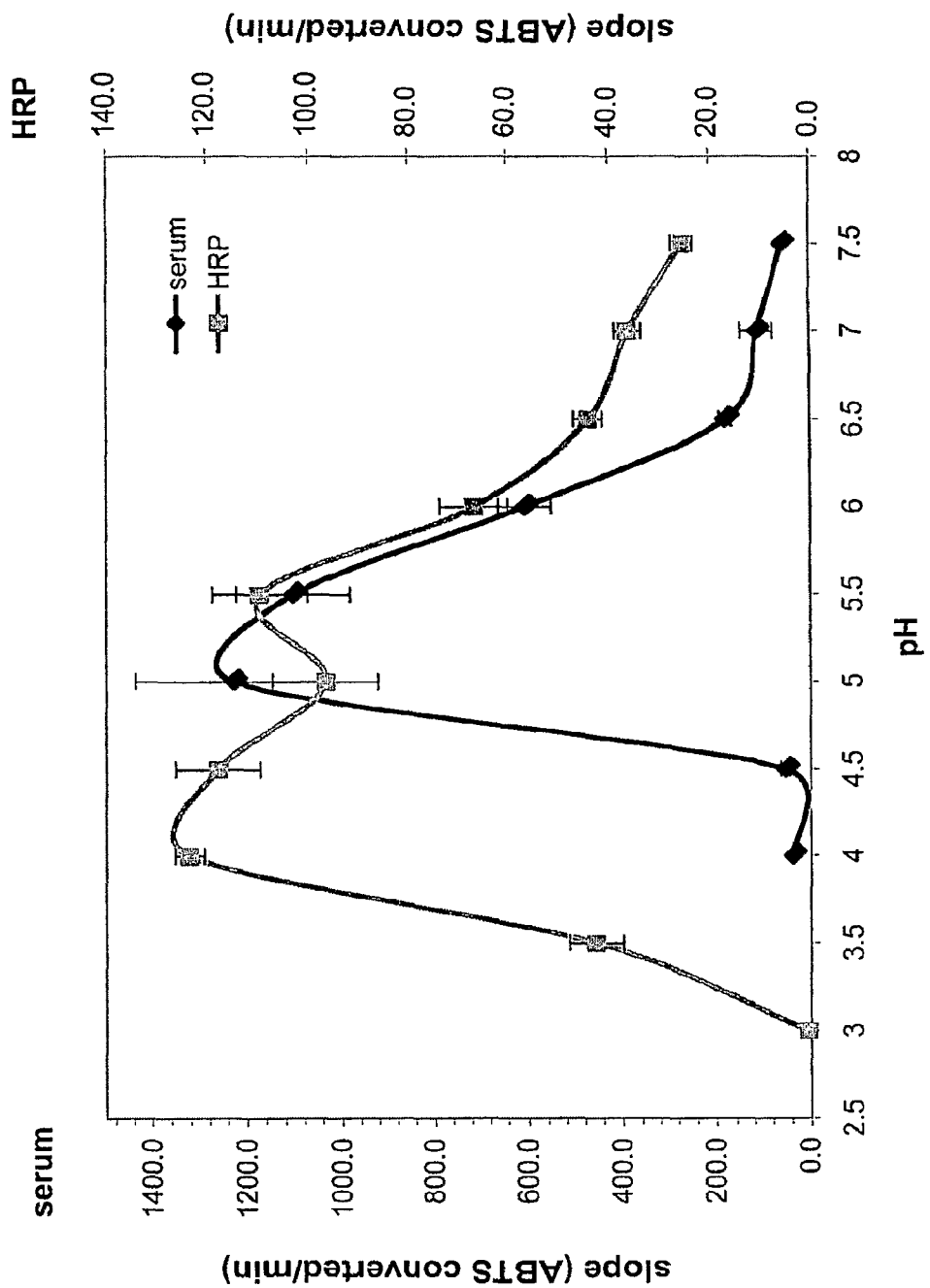
FIG. 10 is a graph of the demonstrating the removal of endogenous peroxidase activity of blood by shifting the pH of the assay conditions to favor the activity of HRP (pH 4.0). The graph demonstrates that at a low pH, HRP strongly reacts with the ABTS substrate whereas the peroxidase activity from blood is minimal.

FIG. 10 demonstrates that the endogenous peroxidase activity of blood can also be removed by shifting the pH of the assay conditions to favor the activity of HRP, an enzyme used in diagnostic assays (for example to pH 4.0). At a low pH, HRP strongly reacts with the ABTS substrate whereas the peroxidase activity from blood is minimal.

Whole rabbit blood was diluted 1:500 in buffers of different pH and incubated for 5 minutes at room temperature. The solution was then spin filtered to remove the cells and 100 µl (microliters) of this diluted serum solution was incubated with 100 µl (microliters) of ABTS. The reaction was monitored for 5 minutes measuring the absorbance at 405 nm in a spectrophotometer. In FIG. 10, the peroxidase activity of the rabbit blood at various pH values is directly compared with that of 1 ng of HRP standard.

In some embodiments, the invention includes a method of removing peroxidase activity in a sample comprising shifting the pH in said sample, thereby removing said peroxidase activity.

All references cited herein are incorporated herein by reference in their entirety.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of removing at least one interferent from a sample comprising contacting a peptide to said sample, thereby removing said interferent, wherein the interferent comprises elastase and wherein said elastase is capable of detection by a peptide comprising the amino acid sequence PFPQANYITY (SEQ ID NO. 1).

2. The method of claim 1, wherein said sample is selected from the group consisting of wound, tissue, urine, saliva, blood, and stool samples.

3. The method of claim 1, wherein said sample is selected from the group consisting of fluid, biopsy and solid samples.

4. The method of claim 1, wherein said interferent is removed prior to an immunostaining or a PCR reaction.

5. The method of claim 1, wherein said peptide is applied to a gauze, cleansing wipe, bead, glass frit, swab, wipe, pad, membrane, a non-woven fiber, a sponge, a filter, or a dressing prior to contact to said sample.

6. The method of claim 1, wherein said peptide is incorporated into a biopsy punch device prior to contact to said sample.

7. The method of claim 1, wherein said peptide is applied to a lateral flow assay device prior to contact to said sample.

8. The method of claim 1, wherein said peptide is incorporated into a collection container, a collection device, a tube, a vial, or a cassette prior to diagnostic testing.

9. A method of removing at least one interferent from a sample comprising contacting a peptide to said sample, thereby removing said interferent, wherein the interferent comprises papain wherein said papain is capable of detection by a peptide comprising the amino add sequence of PMPPLCTSM (SEQ ID NO. 2).

10. The method of claim 9, wherein said sample is selected from the group consisting of wound, tissue, urine, saliva, blood, and stool samples.

11. The method of claim 9, wherein said sample is selected from the group consisting of fluid, biopsy and solid samples.

12. The method of claim 9, wherein said interferent is removed prior to an immunostaining or a PCR reaction.

13. The method of claim 1, wherein said papain is applied to a gauze, cleansing wipe, bead, glass frit, swab, wipe, pad, membrane, a non-woven fiber, a sponge, a filter, or a dressing prior to contact to said sample.

14. The method of claim 1, wherein said papain is incorporated into a biopsy punch device prior to contact to said sample.

15. The method of claim 1, wherein said papain is applied to a lateral flow assay device prior to contact to said sample.

16. The method of claim 1, wherein said papain is incorporated into a collection container, a collection device, a tube, a vial, or a cassette prior to diagnostic testing.

17. A method of removing at least one interferent from a sample comprising contacting a peptide to said sample, thereby removing said interferent, wherein the interferent comprises elastase, and wherein the peptide is capable of detection by a peptide comprising amino acid sequence $H_2N$-PFPQANYITYCV-OH (SEQ ID No:9).

18. The method of claim 17, wherein said sample is selected from the group consisting of wound, tissue, urine, saliva, blood, and stool samples.

19. The method of claim 17, wherein said sample is selected from the group consisting of fluid, biopsy and solid samples.

20. The method of claim 17, wherein said interferent is removed prior to an immunostaining or a PCR reaction.

21. The method of claim 17, wherein said peptide is applied to a gauze, cleansing wipe, bead, glass frit, swab, wipe, pad, membrane, a non-woven fiber, a sponge, a filter, or a dressing prior to contact to said sample.

22. The method of claim 17, wherein said peptide is incorporated into a biopsy punch device prior to contact to said sample.

23. The method of claim 17, wherein said peptide is applied to a lateral flow assay device prior to contact to said sample.

24. The method of claim 17, wherein said peptide is incorporated into a collection container, a collection device, a tube, a vial, or a cassette prior to diagnostic testing.

25. A method of removing at least one interferent from a sample comprising contacting a peptide to said sample, thereby removing said interferent, wherein the interferent comprises papain and wherein said papain is capable of detection by a peptide comprising the amino acid sequence ($NH_2$-E(Edans)PMPPLCTSMK(Dabcyl)-COOH) (SEQ ID No:10).

26. The method of claim 25, wherein said sample is selected from the group consisting of wound, tissue, urine, saliva, blood, and stool samples.

27. The method of claim 25, wherein said sample is selected from the group consisting of fluid, biopsy and solid samples.

28. The method of claim 25, wherein said interferent is removed prior to an immunostaining or a PCR reaction.

29. The method of claim 25, wherein said cation material or phosphocel iulose is applied to a gauze, cleansing wipe, bead, glass frit, swab, wipe, pad, membrane, a non-woven fiber, a sponge, a filter, or a dressing prior to contact to said sample.

30. The method of claim 25, wherein said peptide is incorporated into a biopsy punch device prior to contact to said sample.

31. The method of claim 25, wherein said peptide is applied to a lateral flow assay device prior to contact to said sample.

32. The method of claim 25, wherein said peptide membrane or phosphocellulose is incorporated into a collection container, a collection device, a tube, a vial, or a cassette prior to diagnostic testing.

* * * * *